United States Patent [19]
Seitz et al.

[11] Patent Number: 5,935,979
[45] Date of Patent: Aug. 10, 1999

[54] AMINO ACID AMIDE DERIVATIVES AND THEIR USE AS PESTICIDES

[75] Inventors: Thomas Seitz, Langenfeld; Gerd Hänssler, Leverkusen; Klaus Stenzel, Düsseldorf, all of Germany

[73] Assignee: Bayer Aktiengesellschaft, Leverkusen, Germany

[21] Appl. No.: 08/875,035

[22] PCT Filed: Jan. 10, 1996

[86] PCT No.: PCT/EP96/00071

§ 371 Date: Jul. 16, 1997

§ 102(e) Date: Jul. 16, 1997

[87] PCT Pub. No.: WO96/22970

PCT Pub. Date: Aug. 1, 1996

[30] Foreign Application Priority Data

Jan. 23, 1995 [DE] Germany ............... 195 01 841

[51] Int. Cl.⁶ .................. C07D 213/40; A01N 43/40
[52] U.S. Cl. ............. 514/357; 514/469; 514/616; 546/335; 549/467; 564/152; 564/155
[58] Field of Search .................. 546/334, 335; 514/357, 469, 616; 549/467; 564/152, 155

[56] References Cited

FOREIGN PATENT DOCUMENTS 398072  11/1990  European Pat. Off. .
425925   5/1991  European Pat. Off. .
554729   8/1993  European Pat. Off. .

OTHER PUBLICATIONS

Bull. Chem. Soc. Jpn. (1993), 66(7), 2048–53, XP002001309, Shin, Chugn Gi, et al., "Dehydrooligopeptides. XV. Useful syntheses of dehydrodipeptides by the enzymic coupling of. alpha–dehydroglutamate . . . proteases".

Bull. Chem. Soc. Jpn. (1980), 53(10), 2905–9, XP002001312, Yonezawa, Yasuchika, et al. "Dehydrooligopeptides. I. The facile coupling of .alpha.–dehydroamino acids with . . . dehydrodipeptides".

Chemical Abstracts, vol. 118, No. 21, May 24, 1993, Abstract No. 212719, Ueda, Y. et al. "Synthesis of alpha.–(S)–acylamino–N–(hydroxydioxocyc . . . antibiotics".

Chemical Abstracts, vol. 110, No. 21, May 22, 1989, Abstract No. 193407, Shin Shigeki, et al. "A process for preparation . . . them".

Bull. Chem. Soc. JPN. (1988), 61(7), 2687–9, XP002001310, Yonezawa, Yasuchika, et al. "Dehydrooligopeptides. IX. Syntheses and conversions . . . dipeptides".

Bull Chem. Soc. JPN. (1986), 59(11), 3573–9, XP002001311, Shin, Chung Gi, et al. "Dehydrooligopeptides. VII. Convenient synthesis . . . anhydride".

Bull. Chem. Soc. JPN. (1995), 68(12), 3549–55, XP002001313, Shin, Chung–Gi, et al. "Dehydrooligopeptides. XVIII. Enzymic . . . papain".

Ueda et al, Chemical Abstracts vol. 118, No. 21, No. 212, 719, May 24, 1993.

Shin et al. Chemical Abstracts vol. 110, No. 21, No. 193, 407, May 22, 1989.

Yonezawa et al, Bull. Chem. Soc. Jpn, vol. 53, No. 10, pp. 2905–2909, 1980.

*Primary Examiner*—Zinna Northington Davis
*Attorney, Agent, or Firm*—Sprung Kramer Schaefer & Briscoe

[57] ABSTRACT

The invention relates to novel substituted amino acid amides, to a process for their preparation and to their use as pesticides.

11 Claims, No Drawings

AMINO ACID AMIDE DERIVATIVES AND THEIR USE AS PESTICIDES

This application is a 371 of PCT/EP96/00071 filed Jan. 10, 1996.

The invention relates to novel substituted amino acid amides, to a process for their preparation and to their use as pesticides.

It is known that certain substituted amino acid amides such as, for example, the compound N-(t-butyloxycarbonyl)-L-valine-[N-(1-phenylethyl)-amide] or the compound N-(t-butyloxycarbonyl)-L-valine-{N-[1-(2-chlorophenyl)ethyl]-amide}or the compound N-(t-butyloxycarbonyl)-L-valine-{N-methyl-N-[1-(4-chlorophenyl)-ethyl]-amide} have fungicidal properties (cf. for example EP 398 072).

However, the activity of these prior art compounds is, in particular at low application rates and concentrations, not entirely satisfactory in all areas of application.

This invention accordingly provides the novel amino acid amides of the general formula (I)

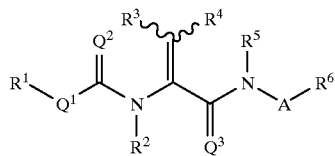

(I)

in which
- A represents a single bond or optionally substituted alkylene,
- $Q^1$, $Q^2$, $Q^3$ are identical or different and each represent oxygen or sulphur,
- $R^1$ represents respectively optionally substituted alkyl, alkenyl, alkinyl, cycloalkyl, cycloalkenyl, arylalkyl, aryl, heterocyclylalkyl or heterocyclyl,
- $R^2$, $R^5$ are identical or different and each represent hydrogen or respectively optionally substituted alkyl,
- $R^3$ represents hydrogen, or respectively optionally substituted alkyl or cycloalkyl,
- $R^4$ represents respectively optionally substituted alkyl or cycloalkyl, or
- $R^3$ and $R^4$ together with the carbon atom that they are attached to form an optionally substituted carbocyclic ring and
- $R^6$ represents respectively optionally substituted cyloalkyl, cycloalkenyl, aryl or heterocyclyl.

In the definitions, the saturated or unsaturated hydrocarbon chains, such as alkyl, alkanediyl, alkenyl or alkinyl, also in connection with hetero atoms, such as in alkoxy, alkylthio or alkylamino, are in each case straight-chain or branched.

Halogen generally represents fluorine, chlorine, bromine or iodine, preferably fluorine, chlorine or bromine, in particular fluorine or chlorine.

Aryl represents aromatic, mono or polycyclic hydrocarbon rings, such as, for example, phenyl, naphthyl, anthranyl, phenanthryl, preferably phenyl or naphthyl, in particular phenyl.

Heterocyclyl represents saturated or unsaturated and aromatic compounds in the form of a ring in which at least one ring member is a hetero atom, i.e. an atom that is different from carbon. If the ring contains more than one hetero atoms, these may be identical or different. Preferred hetero atoms are oxygen, nitrogen or sulphur. The compounds in the form of a ring together with further carbocyclic or heterocyclic, fused or bridged rings optionally form a polycyclic ring system. Preference is given to mono- or bicyclic ring systems, in particular to mono- or bicyclic aromatic ring systems.

Cycloalkyl represents saturated carbocyclic compounds in the form of a ring which together with further carbocyclic, fused or bridged rings optionally form a polycyclic ring system.

Cycloalkenyl represents carbocyclic compounds in the form of a ring which contain at least one double bond and which together with further carbocyclic, fused or bridged rings optionally form a polycyclic ring system.

Furthermore, it was found that the novel amino acid amides of the general formula (I) are obtained when N-substituted amino acids of the general formula (II)

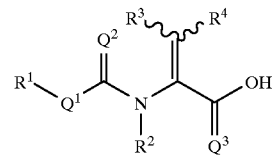

(II)

in which
$Q^1$, $Q^2$, $Q^3$, $R^1$, $R^2$, $R^3$ and $R^4$ are each as defined above are reacted with amines of the general formula (III),

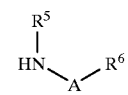

(III)

in which
A, $R^5$ and $R^6$ are each as defined above, if appropriate in the presence of a reaction auxiliary and if appropriate in the presence of a diluent.

Finally, it was found that the novel amino acid amides of the general formula (I) have a very strong fungicidal activity.

The compounds according to the invention may be present as mixtures of different possible isomeric forms, in particular of stereoisomers, such as, for example, E and Z, threo and erythro, and optical isomers. What is claimed includes both the E and the Z isomers, and also the threo and erythro and the optical isomers and any mixtures of these isomers.

The invention preferably provides compounds of the formula (I) in which

A represents a single bond or alkylene having 1 to 6 carbon atoms which is optionally mono- or polysubstituted by identical or different substituents, the possible substituents preferably being selected from the following list:
halogen, cyano, nitro, amino, hydroxyl, formyl, carboxyl, carbamoyl, thiocarbamoyl;
respectively straight-chain or branched alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

cycloalkyl having 3 to 6 carbon atoms;

and aryl or heterocyclyl which is in each case optionally mono- or polysubstituted by identical or different substituents from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and alkylene or dioxyalkylene having in each case 1 to 6 carbon atoms which is in each case attached twice and optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms.

$Q^1$, $Q^2$, $Q^3$ are identical or different and each represent oxygen or sulphur, $R^1$ represents alkyl having 1 to 8 carbon atoms which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

or represents respectively optionally halogen-substituted alkenyl or alkinyl having in each case up to 8 carbon atoms;

or represents cycloalkyl or cycloalkenyl having 3 to 7 carbon atoms which is respectively optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

or represents aryl, arylalkyl or heterocyclyl having 3 to 12 ring members which is respectively optionally mono- or polysubstituted by identical or different substituents, the possible substituents preferably being selected from the following list:
halogen, cyano, nitro, amino, hydroxyl, formyl, carboxyl, carbamoyl, thiocarbamoyl;
respectively straight-chain or branched alkyl, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

alkylene or dioxyalkylene having in each case 1 to 6 carbon atoms which is in each case attached twice and in each case optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and alkylene or dioxyalkylene having in each case 1 to 6 carbon atoms which is in each case attached twice and optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms.

$R^2$, $R^5$ are identical or different and each represent hydrogen or represent alkyl having 1 to 4 carbon atoms or cycloalkyl having 3 to 6 carbon atoms each of which is optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen), $R^3$ represents hydrogen, or represents alkyl having 1 to 8 carbon atoms which is in each case optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

or represents respectively optionally halogen-substituted alkenyl or alkinyl having in each case up to 8 carbon atoms;

or represents cycloalkyl having 3 to 6 carbon atoms, which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl, $R^4$ represents alkyl having 1 to 8 carbon atoms which is in each case optionally mono- or polysubstituted by identical or different substituents from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

or represents respectively optionally halogen-substituted alkenyl or alkinyl having in each case up to 8 carbon atoms;

or represents cycloalkyl having 3 to 6 carbon atoms which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl, or $R^3$ and $R^4$ together with carbon atom that they are attached to form a carbocyclic ring having 3 to 8 carbon atoms which is optionally mono- or polysubstituted by identical or different substituents from the group consisting of halogen, cyano, hydroxyl, amino, $C_1$–$C_4$-alkyl, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen) and $R^6$ represents cycloalkyl or cycloalkenyl having 3 to 8 carbon atoms which is in each case optionally mono- or polysubstituted by identical or different substituents from the group consisting of halogen, cyano, carboxyl, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

or represents aryl or heterocyclyl having 3 to 12 ring members, each of which is optionally mono- or polysubstituted by identical or different substituents, the possible substituents preferably being selected from the following list:

halogen, cyano, nitro, amino, hydroxyl, formyl, carboxyl, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 13 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties;

alkylene or dioxyalkylene having in each case 1 to 6 carbon atoms which is in each case attached twice and in each case optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms which is in each case attached twice and optionally mono- or polysubstituted by identical or different substituents from the group consisting of halogen and straight-chain or branched alkyl having 1 to 4 carbon atoms and straight-chain or branched halogenoalkyl having 1 to 4 carbon atoms and 1 to 9 identical or different halogen atoms.

The invention in particular provides compounds of the formula (I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano, methoxy, phenyl, tolyl, ethylphenyl, methoxyphenyl, ethoxyphenyl, chlorophenyl, fluorophenyl, trifluoromethylphenyl or xylyl, $Q^1$, $Q^2$, $Q^3$ are identical or different and each represent oxygen or sulphur, $R^1$ represents methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl (each of which is optionally substituted by fluorine and/or chlorine), or represents allyl, crotonyl, 1-methyl-allyl, propargyl or 1-methylpropargyl, each of which is optionally mono- to trisubstituted by fluorine, chlorine or bromine;

or represents cyclopropyl, cyclobutyl, cyclopentyl or cyclohexyl, each of which is optionally mono- to hexasubstituted by fluorine, chlorine, bromine, methoxy, ethoxy, cyano, carboxyl, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl, methoxy-carbonyl or ethoxy-carbonyl;

or represents respectively optionally mono- to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl;

trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

$R^2$, $R^5$ are identical or different and each represent hydrogen or represent methyl, ethyl, n- or i-propyl, n-, i-, s- or t-butyl, $R^3$ represents hydrogen or represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl (each of which is optionally substituted by fluorine and/or chlorine), or represents allyl, crotonyl, 1-methyl-allyl, propargyl or 1-methylpropargyl, each of which is optionally mono- to trisubstituted by fluorine, chlorine or bromine;

or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl, $R^4$ represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl (each of which are optionally substituted by fluorine and/or chlorine), or represents allyl, crotonyl, 1-methyl-allyl, propargyl, or 1-methylpropargyl, each of which is optionally mono- to trisubstituted by fluorine, chlorine or bromine;

or represents cylopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl, or $R^3$ and $R^4$ together with the carbon atom that they are attached to represent cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl and $R^6$ represents cyclopropyl, cyclobutyl, cyclopentyl or cyclohexyl, each of which is optionally mono- to hexasubstituted by fluorine, chlorine, bromine, cyano, carboxyl, methyl, ethyl, methoxy, ethoxy, n- or i-propyl, methoxy-carbonyl or ethoxy-carbonyl;

or represents respectively optionally mono- to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl;

trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

Preference is given to compounds of the formula (I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents from the group consisting of fluorine, chlorine, cyano, methoxy, phenyl, tolyl, ethylphenyl, methoxyphenyl, ethoxyphenyl, chlorophenyl, fluorophenyl, trifluoromethylhenyl or xylyl, $Q^1$, $Q^2$, $Q^3$ are identical or different and each represent oxygen or sulphur, $R^1$ represents methyl, ethyl, n- or i-propyl, n-, i-, s- or t-butyl, each of which is optionally mono- to trisubstituted by fluorine, chlorine, bromine, methoxy, ethoxy, methylthio, ethylthio (each of which is optionally substituted by fluorine and/or chlorine),
- or represents allyl, crotonyl, 1-methyl-allyl, propargyl or 1-methylpropargyl, each of which is optionally mono- to trisubstituted by fluorine or chlorine;
- or represents cyclobutyl, cyclopentyl or cyclohexyl, each of which is optionally mono- to hexa substituted by fluorine, chlorine, bromine, methoxy, ethoxy, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl;
- or represents respectively optionally mono- to trisubstituted phenyl, naphthyl, benzyl, furyl, benzofuranyl, thienyl, benzothienyl, pyridyl, quinolyl, tetrahydrofuryl or perhydropyranyl, the possible substituents preferably being selected from the following list:
  fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluorom ethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl;
  trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl, $R^2$, $R^5$ are identical or different and each represent hydrogen or represent methyl, $R^3$ represents hydrogen or represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl (each of which is optionally substituted by fluorine and/or chlorine),
- or represents allyl, crotonyl, 1-methyl-allyl, propargyl, or 1-methylpropargyl, each of which is optionally mono- to trisubstituted by fluorine, chlorine or bromine;
- or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl, $R^4$ represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl (each of which is optionally substituted by fluorine and/or chlorine),
- or represents allyl, crotonyl, 1-methyl-allyl, propargyl or 1-methylpropargyl, each of which is optionally mono- to trisubstituted by fluorine, chlorine or bromine;
- or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl, $R^3$ and $R^4$ together with the carbon atom that they are attached to represent cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl and $R^6$ represents cyclopropyl, cyclobutyl, cyclopentyl or cyclohexyl, each of which is optionally mono- to hexasubstituted by fluorine, chlorine, bromine, cyano, carboxyl, methyl, ethyl, methoxy, ethoxy, n- or i-propyl, methoxy-carbonyl or ethoxy-carbonyl;
- or represents respectively optionally mono- to trisubstituted phenyl, naphthyl, benzyl, phenethyl, furyl, benzofluranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the possible substituents preferably being selected from the following list:
  fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl;
  trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl, cyclopropyl, cyclobutyl, cyclopentyl or cyclohexyl.

A very particularly preferred group of compounds according to the invention are those compounds of the formula (I) in which A represents a single bond or represents methylene, 1,1-ethylene, 1,2-ethylene, 1,1-propylene, 1,2-propylene or 2,2-propylene, $Q^1$, $Q^2$, $Q^3$ each represent oxygen, $R^1$ represents methyl, ethyl, n- or i-propyl, n-, i-, s- or t-butyl, cyclopentyl, cyclohexyl or represents optionally methyl-, ethyl-, methoxy-, ethoxy-, bromine-, chlorine- or fluorine-substituted phenyl or benzyl, $R^2$, $R^5$ each represent hydrogen, $R^3$ represents hydrogen, methyl, ethyl or cyclopropyl, $R^4$ represents methyl, ethyl or cyclopropyl, or $R^3$ and $R^4$ together with the carbon atom that they are attached to form a cyclopentane or cyclohexane ring and $R^6$ represents cyclohexyl which is in each case optionally mono- or disubstituted by methyl, ethyl, methoxy or ethoxy;

or represents phenyl, naphthyl, furyl, benzofuranyl, pyrrolyl, indolyl, thienyl, benzothienyl, pyridyl, quinolyl, pyrimidyl, pyridazinyl, pyrazinyl, each of which is optionally mono- to trisubstituted, the possible substituents preferably being selected from the following list:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl;

trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl.

The abovementioned general or preferred radical definitions apply both to the end products of the formula (I) and, correspondingly, to the starting materials or intermediates required in each case for preparation.

These radical definitions can be combined with each other as desired, that is to say combinations between the ranges stated for preferred compounds are also possible.

The amino acid derivates required as starting materials to carry out the process according to the invention are defined in the general way by the formula (II). In this formula (II), $Q^1$, $Q^2$, $Q^3$, $R^1$, $R^2$, $R^3$ and $R^4$ each preferably or in particular have those meanings already given in connection with the description of the compounds of the formula (I) according to the invention as preferred or as particularly preferred for $Q^1$, $Q^2$, $Q^3$, $R^1$, $R^2$, $R^3$ and $R^4$.

The starting materials of the formula (II) are known and/or can be prepared by known processes (cf for example Shin, Chung, Gi; et al. Chem. Pharm. Bull. 1984, 3934–3944).

The amines further required as starting materials to carry out the process according to the invention are defined in the general way by the formula (III). In this formula (III), A, $R^5$ and $R^6$ each preferably or in particular have those meanings already given in connection with the description of the compounds of the formula (I) according to the invention as preferred or as particularly preferred for A, $R^5$ and $R^6$.

The amines of the general formula (III) are known reagents in organic chemistry.

The process according to the invention is, if appropriate, carried out in the presence of a diluent. Suitable diluents for carrying out the process according to the invention are all inert organic solvents. These are preferably aliphatic, alicyclic or aromatic hydrocarbons, such as, for example, petroleum ether, hexane, heptane, cyclohexane, methylcyclohexane, benzene, toluene, xylene or decahydronapthalene; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketons, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide or sulphones such as sulpholane.

The process according to the invention is, if appropriate, carried out in the presence of a suitable condensing agent. Suitable condensing agents are all condensing agents customarily used for such amidation reactions. Examples include acyl halide formers such as phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride; carbodiimides, such as N,N'-dicyclohexylcarbodiimide (DCC) or other conventional condensingagents, such as phosphorus pentoxide, polyphosphoric acid, N,N'carbonyldiimidazole, 2-ethoxy-N-ethoxycarbonyl-1,2-dihydroquinoline (EEDQ) or triphenylphosphine/carbon tetrachloride.

The process according to the invention is, if appropriate, carried out in the presence of a suitable acid acceptor. Suitable acid acceptors are all conventional inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process according to the invention is, if appropriate, carried out in the presence of a catalyst. Examples include 4-dimethylaminopyridine, 1-hydroxybenzotriazole and dimethylformamide.

When carrying out the process according to the invention, the reaction temperatures may be varied over a relatively wide range. In general, temperatures between −78° C. and +120° C., preferably temperatures between −60° C. and +25° C., are employed.

In the practice of the process according to the invention for preparing compounds of the formula (I), generally 0.5 to 5 mol, preferably equimolar amounts, of amine of the formula (III) are employed per mole of the amino acid derivative of the formula (II).

The reaction is carried out and the reaction products are worked up and isolated according to known processes (cf. the preparation examples).

The process according to the invention may also be carried out as a two-step process. For this purpose, the amino acid derivatives of the general formula (II) are initially converted into an activated form and reacted with the amines of the general formula (III) in a subsequent step to give the amino acid amides of the general formula (I) according to the invention.

Suitable activated forms of the amino acid derivatives of the formula (II) are all carboxy-activated derivatives, such as, for example, acyl halides, preferably acyl chlorides, acyl azides, further symmetric and mixed anhydrides, such as, for example, the mixed O-alkylcarbonic anhydrides, furthermore activated esters, such as, for example, p-nitrophenyl esters or N-hydroxy-succinimide esters and adducts with condensing agents, such as, for example, dicyclohexylcarbodiimide or activated forms of the amino acids prepared in situ.

In the practice of the two-step process, preference is given to using the acyl chlorides and mixed anhydrides corresponding to the amino acids of the formula (II). They can be prepared by reacting the amino acids of the formula (II) or salts thereof in a conventional manner with a halogenating agent or one of the conventional agents for preparing mixed anhydrides, such as, for example, phosphorus pentachloride, thionyl chloride, oxalyl chloride or chloroformates.

The two steps of the two-step process are each, if appropriate, carried out in the presence of a diluent and, if appropriate, in the presence of a catalyst. Preferred diluents and catalysts are those diluents and catalysts already mentioned in connection with the description of the one-step process.

The reaction is carried out and the reaction products are worked up and isolated according to known processes. The compounds according to the invention have a potent microbicidal activity and are employed for controlling undesirable microorganisms. The compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidial form: Drechslera, synonym: Helminthosporium);

Cochliobolus species, such as, for example, *Cochliobolus sativus* (conidial form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture, fruit growing and horticulture, such as for example, against Plasmopara species and Phytophthora species.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example allylaryl polyglycol ethers, alkylsulphonates, alkyl sulphates, arylsulphonates, or else protein hydrolysates; suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations, also as a mixture with known fungicides, bactericides, acaricides, nematicides or insecticides in order thus, for example, to widen the spectrum of action or to prevent development of resistance.

In many cases, synergistic effects are observed.
Examples of co-components in mixtures are:
Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide;
2,6-dichloro-N-(4-trifluoromethylbenzyl)benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]phenyl}3-methoxyacrylate; methyl (E)-methoximino[alpha-(o-tolyloxy)-o-tolyl]acetate; 2-phenylphenol (OPP), aldimorph, ampropylfos, anilazine, azaconazole,
benalaxyl, benodanil, benomyl, binapacryl, biphenyl, bitertanol, blasticidin-S, bromuconazole, bupirimate, buthiobate,
calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon,
edifenphos, epoxyconazole, ethirimol, etridiazole,
fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox,
guazatine,
hexachlorobenzene, hexaconazole, hymexazol,
imazalil, imibenconazole, iminoctadine, iprobenfos (IBP), iprodione, isoprothiolane,
kasugamycin, copper preparations such as: copper hydroxide, copper naphthenate, copper oxychloride, copper sulphate, copper oxide, oxine-copper and Bordeaux mixture,
mancopper, mancozeb, maneb, mepanipyrim, mepronil, metalaxyl, metconazole, methasulfocarb, methfuroxam, metiram, metsulfovax, myclobutanil,
nickel dimethyldithiocarbamate, nitrothal-isopropyl, nuarimol,
ofurace, oxadixyl, oxamocarb, oxycarboxin,
pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.
Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,
*Bacillus thuringiensis*, bendiocarb, benfuracarb, bensultap, betacyluthrin, bifenthrin, BPMC, brofenprox, bromophos A, bufencarb, buprofezin, butocarboxim, butylpyridaben,
cadusafos, carbaryl, carbofuran, carbophenothion, carbosulphan, cartap, CGA 157419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phosphamdon, phoxim, pirimicarb, pirimiphos M, primiphos A, profenofos, profenophos, promecarb, propaphos, propoxur, prothiofos, prothiophos, prothoate, pymetrozin, pyraclophos, pyrachlofos, pyraclophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to admix the active compounds according to the invention with other known active compounds, such as herbicides, or else with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range: They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

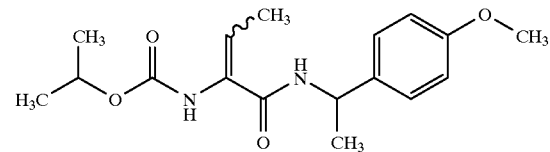

At $-20°$ C., 0.5 g (0.005 mol) of N-methylpiperidine and then, dropwise with stirring at $-20°$ C., 0.7 g (0.005 mol) of isobutyl chloroformate are added to 1.0 g (0.005 mol) of 2-(i-propoxycarbonylamino)-but-2-enoic acid in 10 ml of dichloromethane. After the addition is complete, stirring is continued at $-20°$ C. for a further 10 minutes, and 0.75 g (0.005 mol) of 1-(4-methoxyphenyl)-ethylamine are added, the temperature being kept below $-15°$ C. Stirring is then continued for a further 2 hours at $-15°$ C. and for 15 hours at room temperature, the precipitated solid is filtered off and washed with dichloromethane, the filtrate is concentrated under reduced pressure, the residue is taken up in water and extracted repeatedly with ethyl acetate, the combined organic phases are washed with aqueous sodium bicarbonate solution and water and dried over sodium sulphate, and the solvent is removed under reduced pressure. 0.8 g (47% of theory) of N-[1-(4-methoxyphenyl)-ethyl]-2-(i-propoxycarbonylamino)-but-2-enoic acid amide are obtained as a colourless oil. $^1$H-NMR (CDCl$_3$, TMS), δ (ppm): 1.25 (m, 6H), 1.50 (d, 3H); 1.74 (d, 3H); 3.79 (s, 3H).

TABLE 1

| Ex. No. | R$^1$ | R$^3$ | R$^4$ | A | R$^6$ | physical constant |
|---|---|---|---|---|---|---|
| (2) | —CH(CH$_3$)$_2$ | —CH$_3$ | —CH$_3$ | 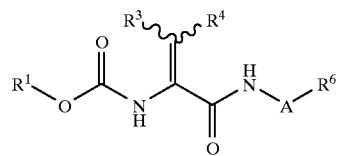 | ⟨4-Cl-C$_6$H$_4$⟩ | m.p.: 210° C. |

TABLE 1-continued

Structure: R¹—O—C(=O)—NH—C(=CR³R⁴)—C(=O)—NH—A—R⁶

| Ex. No. | R¹ | R³ | R⁴ | A | R⁶ | physical constant |
|---|---|---|---|---|---|---|
| (3) | —CH(CH₃)₂ | —CH₃ | —CH₃ | — | cyclohexyl | m.p.: 180° C. |
| (4) | —CH(CH₃)₂ | —CH₃ | —CH₃ | —CH₂— | 4-Cl-phenyl | m.p.: 130° C. |
| (5) | —CH(CH₃)₂ | —CH₃ | H | — | 4-Cl-phenyl | m.p.: 184° C. |
| (6) | —CH(CH₃)₂ | —CH₃ | H | —CH₂— | 4-Cl-phenyl | m.p.: 100° C. |
| (7) | —CH(CH₃)₂ | —CH₃ | H | — | cyclohexyl | m.p.: 113° C. |
| (8) | —CH(CH₃)₂ | —CH₃ | H | >CH—CH₃ | 4-Cl-phenyl | 1H-NMR*): 1.25 (m, 6H), 1.45(d, 3H), 1.75(d, 3H) |
| (9) | —CH(CH₃)₂ | —CH₃ | H | >CH—CH₃ | 4-F-phenyl | 1H-NMR*): 1.24 (m, 6H), 1.45(d, 3H), 1.75(d, 3H) |
| (10) | —CH(CH₃)₂ | —CH₃ | —CH₃ | >CH—CH₃ | 4-Cl-phenyl | m.p.: 137° C. |
| (11) | —CH(CH₃)₂ | —CH₃ | —CH₃ | >CH—CH₃ | 4-CH₃-phenyl | m.p.: 149° C. |
| (12) | —CH(CH₃)₂ | —CH₃ | —CH₃ | >CH—CH₃ | 4-OCH₃-phenyl | m.p.: 109° C. |

TABLE 1-continued

[Structure: R¹O-C(=O)-NH-C(=CR³R⁴)-C(=O)-NH-A-R⁶]

| Ex. No. | R¹ | R³ | R⁴ | A | R⁶ | physical constant |
|---|---|---|---|---|---|---|
| (13) | —CH(CH₃)₂ | —CH₃ | —CH₃ | >CH—CH₃ | 4-F-C₆H₄— | m.p.: 152° C. |
| (14) | —CH(CH₃)₂ | —CH₃ | —CH₃ | >CH—CH₃ | 3,4-Cl₂-C₆H₃— | m.p.: 124° C. |
| (15) | —CH(CH₃)(C₂H₅) | —CH₃ | —CH₃ | >CH—CH₃ | 4-OCH₃-C₆H₄— | ¹H-NMR*): 0.89 (m, 3H), 1.15(m, 3H), 1.49(d, 3H), 1.76 (s, 3H), 1.99(s, 3H) |
| (16) | —CH(CH₃)(C₂H₅) | —CH₃ | —CH₃ | >CH—CH₃ | 4-F-C₆H₄— | ¹H-NMR*): 0.85 (m, 3H), 1.20(m, 3H), 1.50(d, 3H), 1.77 (s, 3H), 1.99(s, 3H) |
| (17) | —CH(CH₃)(C₂H₅) | —CH₃ | H | >CH—CH₃ | 4-OCH₃-C₆H₄— | ¹H-NMR*): 0.88 (m, 3H), 1.22(m, 3H), 1.50(d, 3H), 1.75(d, 3H) |
| (18) | —CH(CH₃)(C₂H₅) | —CH₃ | H | >CH—CH₃ | 3,4-Cl₂-C₆H₃— | ¹H-NMR*): 0.90 (m, 3H), 1.22(m, 3H), 1.49(d, 3H), 1.78(d, 3H) |
| (19) | —CH(CH₃)₂ | —CH₃ | —CH₃ | >CH—CH₃ | 4-C₂H₅-C₆H₄— | m.p.: 150° C. |
| (20) | —CH(CH₃)₂ | —CH₃ | —CH₃ | >CH—CH₃ | 5-Cl-2-methylbenzofuran-yl | m.p.: 102° C. |
| (21) | —CH(CH₃)₂ | —CH₃ | —CH₃ | >CH—CH₃ (S) | C₆H₅— | m.p.: 150° C. |

TABLE 1-continued $$R^1\text{—}O\text{—}\underset{\underset{H}{|}}{C}(=O)\text{—}N\text{—}\underset{\underset{O}{\parallel}}{C}(R^3)(R^4)\text{—}\overset{\sim}{C}\text{—}N\underset{H}{|}\text{—}A\text{—}R^6$$

| Ex. No. | R₁ | R³ | R⁴ | A | R⁶ | physical constant |
|---|---|---|---|---|---|---|
| (22) | —CH(CH₃)₂ | —CH₃ | —CH₃ | >CH—CH₃ | 3-pyridyl | m.p.: 150° C. |
| (23) | —CH(CH₃)(C₂H₅) | —CH₃ | —CH₃ | >CH—CH₃ (R) | 4-Cl-C₆H₄— | m.p.: 127° C. |
| (24) | —CH(CH₃)(C₂H₅) | —CH₃ | —CH₃ | >CH—CH₃ | 4-CH₃-C₆H₄— | m.p.: 110° C. |
| (25) | —CH(CH₃)(C₂H₅) | —CH₃ | —CH₃ | >CH—CH₃ | 4-C₂H₅-C₆H₄— | m.p.: 106° C. |
| (26) | —CH(CH₃)₂ | —CH₃ | H | >CH—CH₃ | 4-CH₃-C₆H₄— | m.p.: 104° C. |
| (27) | —CH(CH₃)₂ | —CH₃ | H | >CH—CH₃ | 4-C₂H₅-C₆H₄— | m.p.: 111° C. |
| (28) | —CH(CH₃)₂ | —CH₃ | H | >CH—CH₃ | 4-Cl-C₆H₄— | m.p.: 105° C. |
| (29) | —CH(CH₃)(C₂H₅) | —CH₃ | H | >CH—CH₃ (R) | 4-Cl-C₆H₄— | m.p.: 71° C. |
| (30) | —CH(CH₃)(C₂H₅) | —CH₃ | H | >CH—CH₃ | 4-CH₃-C₆H₄— | m.p.: 81° C. |
| (31) | —CH(CH₃)(C₂H₅) | —CH₃ | H | >CH—CH₃ | 4-C₂H₅-C₆H₄— | m.p.: 70° C. |

TABLE 1-continued

| Ex. No. | R¹ | R³ | R⁴ | A | R⁶ | physical constant |
|---|---|---|---|---|---|---|
| (32) | -CH(CH₃)(C₂H₅) | -CH₃ | H | >CH-CH₃ | 4-Cl-C₆H₄- | m.p.: 85° C. |
| (33) | -CH(CH₃)₂ | -CH₃ | -CH₃ | >CH-CH₃ (R) | C₆H₅- | m.p.: 114° C. |
| (34) | -CH(CH₃)(C₂H₅) | -CH₃ | -CH₃ | >CH-CH₃ | 5-chloro-2-methylbenzofuran-yl | m.p.: 106° C. |
| (35) | -CH(CH₃)(C₂H₅) | -CH₃ | -CH₃ | >CH-CH₃ (S) | C₆H₅- | m.p.: 122° C. |
| (36) | -CH(CH₃)(C₂H₅) | -CH₃ | -CH₃ | >CH-CH₃ (R) | C₆H₅- | m.p.: 140° C. |
| (37) | -CH(CH₃)(C₂H₅) | -CH₃ | -CH₃ | >CH-CH₃ | 3,4-Cl₂-C₆H₃- | m.p.: 140° C. |
| (38) | -CH(CH₃)(C₂H₅) | -CH₃ | -CH₃ | >CH-CH₃ | pyridin-3-yl | m.p.: 145° C. |
| (39) | -CH(CH₃)(C₂H₅) | -CH₃ | -CH₃ | >CH-CH₃ | 4-Cl-C₆H₄- | m.p.: 113° C. |
| (40) | -CH(CH₃)₂ | -CH₃ | -CH₃ | -CH₂-CH₂- | 3,4-(OCH₃)₂-C₆H₃- | m.p.: 100° C. |

TABLE 1-continued

Structure: $R^1O-C(=O)-NH-C(=CR^3R^4)-C(=O)-NH-A-R^6$

| Ex. No. | $R^1$ | $R^3$ | $R^4$ | A | $R^6$ | physical constant |
|---|---|---|---|---|---|---|
| (41) | —CH(CH₃)(C₂H₅) | —CH₃ | —CH₃ | —CH₂—CH₂— | 3,4-dimethoxyphenyl | m.p.: 104° C. |
| (42) | —CH(CH₃)₂ | —CH₃ | —CH₃ | —CH(CH₃)—CH₂— | 4-OCH₃-phenyl | m.p.: 109° C. |
| (43) | —CH(CH₃)(C₂H₅) | —CH₃ | —CH₃ | —CH(CH₃)— (isopropyl linker) | 4-OC₂H₅-phenyl | m.p.: 119° C. |
| (44) | —CH(CH₃)(C₂H₅) | —CH₃ | —CH₃ | —C(CH₃)(C₂H₅)— | 4-OCH₃-phenyl | m.p.: 95° C. |
| (45) | —CH(CH₃)(C₂H₅) | —CH₃ | —CH₃ | —CH(CH₃)—CH₂— | 4-OCH₃-phenyl | m.p.: 102° C. |
| (46) | —CH(CH₃)₂ | —CH₃ | —CH₃ | —CH(CH₃)— (isopropyl linker) | 4-OC₂H₅-phenyl | m.p.: 115° C. |
| (47) | —CH(CH₃)(C₂H₅) | —CH₃ | —CH₃ | —CH(CH₃)—CH₂—CH₂— | 4-OCH₃-phenyl | m.p.: 100° C. |
| (48) | —CH(CH₃)(C₂H₅) | —CH₃ | —CH₃ | —CH(CH₃)— (isopropyl linker) | 3-OCH₃-phenyl | ¹H-NMR*⁾: 3.80(s, 3H) |
| (49) | —CH(CH₃)(C₂H₅) | —CH₃ | —CH₃ | —CH(CH₃)— (isopropyl linker) | 3-CF₃-phenyl | m.p.: 96° C. |

TABLE 1-continued

Structure:
$$R^1-O-C(=O)-N(H)-C(R^3)=C(R^4)-C(=O)-N(H)-A-R^6$$

| Ex. No. | R₁ | R³ | R⁴ | A | R⁶ | physical constant |
|---|---|---|---|---|---|---|
| (50) | —CH(CH₃)₂ | —CH₃ | —CH₃ | >CH—CH₃ | 3-CH₃-phenyl | m.p.: 120° C. |
| (51) | —CH(CH₃)₂ | —CH₃ | —CH₃ | >CH—CH₃ | 3-CF₃-phenyl | m.p.: 127° C. |
| (52) | —CH(CH₃)₂ | —CH₃ | —CH₃ | —CH₂—CH₂— | 4-Cl-phenyl | m.p.: 115° C. |
| (53) | —CH(CH₃)₂ | —CH₃ | —CH₃ | >CH—CH₃ | 2,4-diCl-phenyl | ¹H-NMR*⁾: 1.78(s, 3H), 2.00(s, 3H) |
| (54) | —CH(CH₃)₂ | —CH₃ | —CH₃ | —CH₂—CH₂— | 4-OCH₃-phenyl | m.p.: 126° C. |
| (55) | —CH(CH₃)₂ | —CH₃ | —CH₃ | >CH—CH₃ | cyclohexenyl | m.p.: 155° C. |
| (56) | —CH(CH₃)(C₂H₅) | —CH₃ | —CH₃ | >CH—CH₃ | cyclohexenyl | m.p.: 134° C. |

*⁾The ¹H-NMR spectra were recorded in deuterochloroform (CDCl₃) or hexa-deuterodimethyl sulphoxide (DMSO-d₆) using tetramethylsilane (TMS) as internal standard. Stated is the chemical shift as d value in ppm.

USE EXAMPLES

Example: A

Plasmopara Test (vines)/Protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for protective acitivity, young plants are sprayed with the preparation of active compound. After the spray coating has dried on, the plants are inoculated with an aqueous spore suspension of plasmopara viticola and then remain in a humid chamber at 20 to 22° C., and 100% relative atmospheric humidity for 1 day. The plants are then placed in a greenhouse at 21° C. and about 90% atmospheric humidity for 5 days. The plants are then moistened and placed in a humid chamber for 1 day.

The test is evaluated 6 days after inoculation.

In this test, for example the following compound (2), (8), (10), (11), (12), (15), (19), (20), (23), (36), (39) and (41)

exhibits an efficacy of more than 90% at an active compound concentration of 100 ppm.

Example B

Phytophthora Test (tomato)/Protective

Solvent: 12.5 parts by weight of acetone

Emulsifer: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound to run-off point. After the spray coating has dried on, the plants are inoculated with an aqueous spore suspension of phytophthora infestans.

The plants remain in an incubation cabin at 100% relative atmospheric humidity and about 20° C.

The test is evaluated 4 days after inoculation.

In this test, for example the following compound (2) of the Preparation Examples exhibits an efficacy of 100% at an active compound concentration of 0.05%.

We claim:

1. A compound of the formula (I)

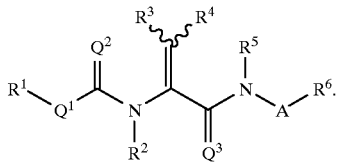

(I)

in which

| A | represents a single bond or alkylene having 1 to 6 carbon atoms which is optionally mono- or polysubstituted by identical or different substituents selected from the group consisting of: halogen, cyano, nitro, amino, hydroxyl, formyl, carboxyl, carbamoyl, thiocarbamoyl; straight-chain or branched alkoxy, alkylthio, alkylsulphinyl or alkylsulphonyl having in each case 1 to 6 carbon atoms; straight-chain or branched alkenyl or alkenyloxy having in each case 2 to 6 carbon atoms; straight-chain or branched halogenoalkoxy, halogenoalkylthio, halogenoalkylsulphinyl or halogenoalkylsulphonyl having in each case 1 to 6 carbon atoms and 1 to 13 identical or different halogen atoms; straight-chain or branched halogenoalkenyl or halogenoalkenyloxy having in each case 2 to 6 carbon atoms and 1 to 13 identical or different halogen atoms; straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties; cycloalkyl having 3 to 6 carbon atoms; and aryl or heterocyclyl which is in each case optionally mono- or polysubstituted by identical or different substituents from the group consisting of: halogen, cyano and straight-chain or branched alkyl having 1 to 4 carbon atoms; straight-chain or branched halogenoalkyl having 1 to 4 carbon atoms and 1 to 9 identical or different halogen atoms; straight-chain or branched alkoxy or alkylthio having 1 to 4 carbon atoms; straight-chain or branched halogenoalkoxy or halogenoalkylthio having 1 to 4 carbon atoms and 1 to 9 identical or different halogen atoms; and alkylene or dioxyalkylene having in each case 1 to 6 carbon atoms which is in each case attached twice and optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms; |
|---|---|
| $Q^1$, $Q^2$, $Q^3$ | are identical or different and each represent oxygen or sulphur; |
| $R^1$ | represents alkyl having 1 to 8 carbon atoms which is optionally mono- or polysubstituted by identical or different substituents from the group consisting of halogen, cyano, hydroxyl, amino, and $C_1$–$C_4$-alkoxy, $C_1$–$C_4$-alkylthio, $C_1$–$C_4$-alkylsulphinyl and C–$C_4$-alkylsulphonyl, each of which may optionally be substituted by halogen; or represents optionally halogen-substituted alkenyl or alkinyl having in each case up to 8 carbon atoms; or represents cycloalkyl or cycloalkenyl having 3 to 7 carbon atoms which is optionally mono- or polysubstituted by identical or different substituents from the group consisting of halogen, cyano, carboxyl, phenyl which is optionally substituted by halogen, cyano, $C_1$–$C_4$-alkyl, $C_1$–$C_4$-halogenoalkyl, $C_1$–$C_4$-alkoxy or C–$C_4$-halogenoalkoxy, $C_1$–$C_4$-alkyl and $C_1$–$C_4$-alkoxy-carbonyl; or represents aryl, arylalkyl or heterocyclyl having 3 to 12 ring members which is optionally mono- or polysubstituted by identical or different substituents, the substituents being selected from the group consisting of: halogen, cyano, nitro, amino, hydroxyl, formyl, carboxyl, carbamoyl, thiocarbamoyl; straight-chain or branched alkyl, alkoxy, alkylthio, alkylsulphinyl or alkylsulphonyl having in each case 1 to 6 carbon atoms; straight-chain or branched alkenyl or alkenyloxy having in each case 2 to 6 carbon atoms; straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms; straight-chain or branched halogenoalkenyl or halogenoalkenyloxy having in each case 2 to 6 carbon atoms and 1 to 13 identical or different halogen atoms; straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties; alkylene or dioxyalkylene having in each case 1 to 6 carbon atoms which is in each case attached twice and in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms; cycloalkyl having 3 to 6 carbon atoms; and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from the group consisting of: halogen, cyano and straight-chain or branched alkyl having 1 to 4 carbon atoms; straight-chain or branched halogenoalkyl having 1 to 4 carbon atoms and 1 to 9 identical or different halogen atoms; straight-chain or branched alkoxy or alkylthio having 1 to 4 carbon atoms; straight-chain or branched halogenoalkoxy or halogenoalkylthio having 1 to 4 carbon atoms and 1 to 9 identical or different halogen atoms; and alkylene or dioxyalkylene having in each case 1 to 6 carbon atoms which is in each case attached twice and optionally mono- or polysubstituted by identical or different substituents from the group consisting of |

| | halogen, straight-chain or branched alkyl having 1 to 4 carbon atoms and straight-chain or branched halogenoalkyl having 1 to 4 carbon atoms and 1 to 9 identical or different halogen atoms; |
|---|---|
| $R^2$, $R^5$ | are identical or different and each represent hydrogen or represent alkyl having 1 to 4 carbon atoms or cycloalkyl having 3 to 6 carbon atoms each of which is optionally mono- or polysubstituted by identical or different substituents from the group consisting of halogen, cyano, hydroxyl, amino, and $C_1$–$C_4$-alkoxy, $C_1$–$C_4$-alkylthio, $C_1$–$C_4$-alkylsulphinyl, $C_1$–$C_4$-alkylsulphonyl, each of which may optionally be substituted by halogen; |
| $R^3$ | represents hydrogen, or represents alkyl having 1 to 8 carbon atoms which is optionally mono- or polysubstituted by identical or different substituents from the group consisting of halogen, cyano, hydroxyl, amino, and $C_1$–$C_4$-alkoxy, $C_1$–$C_4$-alkylthio, $C_1$–$C_4$-alkyl-sulphinyl and $C_1$–$C_4$-alkylsulphonyl each of which may optionally be substituted by halogen; or represents optionally halogen-substituted alkenyl or alkinyl having each case up to 8 carbon atoms; or represents cycloalkyl having 3 to 6 carbon atoms, which is optionally mono- or polysubstituted by identical or different substituents from the group consisting of halogen, cyano, carboxyl, phenyl, which is optionally substituted by halogen, cyano, $C_1$–$C_4$-alkyl, $C_1$–$C_4$-halogenoalkyl, $C_1$–$C_4$-alkoxy, or $C_1$–$C_4$-halogenoalkoxy, $C_1$–$C_4$-alkyl and $C_1$–$C_4$-alkoxy-carbonyl; |
| $R^4$ | represents alkyl having 1 to 8 carbon atoms which is optionally mono- or polysubstituted by identical or different substituents from the group consisting of halogen, cyano, hydroxyl, amino, and $C_1$–$C_4$-alkoxy, $C_1$–$C_4$-alkylthio, $C_1$–$C_4$-alkyl-sulphinyl and $C_1$–$C_4$-alkylsulphonyl, each of which may optionally be substituted by halogen; or represents optionally substituted halogen-substituted alkenyl or alkinyl having in each case up to 8 carbon atoms; or represents cycloalkyl having 3 to 6 carbon atoms which is optionally mono- or polysubstituted by identical or different substituents from the group consisting of halogen, cyano, carboxyl, phenyl, which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy, $C_1$–$C_4$-alkyl and $C_1$–$C_4$-alkoxy-carbonyl; or |
| $R^3$ and $R^4$ | together with carbon atoms that they are attached to form a carbocyclic ring having 3 to 8 carbon atoms which is optionally mono- or polysubstituted by identical or different substituents from the group consisting of halogen, cyano, hydroxyl, amino, and $C_1$–$C_4$-alkyl, $C_1$–$C_4$-alkoxy, $C_1$–$C_4$-alkylthio, $C_1$–$C_4$-alkylsulphinyl and $C_1$–$C_4$-alkylsulphonyl, each of which may optionally be substituted by halogen; and |
| $R^6$ | represents cycloalkyl or cycloalkenyl having 3 to 8 carbon atoms which is in each case optionally mono- or polysubstituted by identical or different substituents from the group consisting of halogen, cyano, carboxyl, phenyl, which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy, $C_1$–$C_4$-alkyl and $C_1$–$C_4$-alkoxy-carbonyl; or represents aryl or heterocyclyl having 3 to 12 ring members, each of which is optionally mono- or polysubstituted by identical or different substituents, the substituents being selected from the group consisting of: halogen, cyano, nitro, amino, hydroxyl, formyl, carboxyl, carbamoyl, thiocarbamoyl; straight-chain or branched alkyl, alkoxy, alkylthio, alkylsulphinyl or alkylsulphonyl having in each case 1 to 6 carbon atoms; straight-chain or branched alkenyl or alkenyloxy having in each case 2 to 6 carbon atoms; straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms; straight-chain or branched halogenoalkenyl or halogenoalkenyloxy having in each case 2 to 6 carbon atoms and 1 to 13 identical or different halogen atoms; straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties; alkylene or dioxyalkylene having in each case 1 to 6 carbon atoms which is in each case attached twice and in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms; cycloalkyl having 3 to 6 carbon atoms; and aryl, aryloxy, arylthio, arylalkyl, arylalyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents from the group consisting of: halogen, cyano and straight-chain or branched alkyl having 1 to 4 carbon atoms; straight-chain or branched halogenoalkyl having 1 to 4 carbon atoms and 1 to 9 identical or different halogen atoms; straight-chain or branched alkoxy or alkylthio having 1 to 4 carbon atoms; straight-chain or branched halogenoalkoxy or halogenoalkylthio having 1 to 4 carbon atoms and 1 to 9 identical or different halogen atoms; and alkylene or dioxyalkylene having in each case 1 to 6 carbon atoms which is in each case attached twice and optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms. |

2. A compound of the formula (I) according to claim 1, in which

| | |
|---|---|
| A | represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene), each of which is optionally mono- or polysubstituted by identical or different substituents from the group consisting of fluorine, chlorine, cyano, methoxy, phenyl, tolyl, ethylphenyl, methoxyphenyl, ethoxyphenyl, chlorophenyl, fluorophenyl, trifluoromethylphenyl or xylyl; |
| $Q^1$, $Q^2$, $Q^3$ | are identical or different and each represent oxygen or sulphur; |
| $R^1$ | represents methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, |

-continued

| | |
|---|---|
| | 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl, each of which is optionally substituted by fluorine and/or chlorine; or represents allyl, crotonyl, 1-methyl-allyl, propargyl or 1-methyl-propargyl, each of which is optionally mono- to trisubstituted by fluorine, chlorine or bromine; or represents cyclopropyl, cyclobutyl, cyclopentyl or cyclohexyl, each of which is optionally mono- to hexasubstituted by fluorine, chlorine, bromine, methoxy, ethoxy, cyano, carboxyl, phenyl, which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, methyl, ethyl, n- or i-propyl, methoxy-carbonyl or ethoxy-carbonyl; or represents optionally mono- to trisubstituted phenyl, naphthyl, benzyl, phenethyl furyl, benzofuranyl, pyrrolyl, indolyl, thienyl, benzothienyl, oxazolyl, isoxazolyl, thiazolyl, isothiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of: fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i- propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl; trimethylene (propane-1,3-diyl), methylenedioxy or ethylenedioxy each of which is attached twice and each of which is optionally mono- or polysubstituted by identical or different substituents from the group consisting of fluorine, chlorine, methyl, trifluoromethyl, ethyl, n- and I-propyl; and cyclopropyl, cyclobutyl, cyclopentyl or cyclohexyl; |
| $R^2, R^5$ | are identical or different and each represent hydrogen or represent methyl, ethyl, n- or i-propyl, n- i-, s- or t-butyl; |
| $R^3$ | represents hydrogen or represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, ethylsulphonyl, each of which is optionally substituted by fluorine and/or chlorine; or represents allyl, crotonyl; 1-methyl-allyl, propargly or 1-methyl-propargyl, each of which is optionally mono- to trisubstituted by fluorine, chlorine or bromine; or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; |
| $R^4$ | represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, or ethylsulphonyl; or represents allyl, crotonyl, 1-methyl-allyl, propargyl or 1-methyl-propargly, each of which is optionally mono- to trisubstituted by fluorine, chlorine or bromine; or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; or |
| $R^3$ and $R^4$ | together with the carbon atom that they are attached to represent cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; and |
| $R^6$ | represents cyclopropyl, cyclobutyl, cyclopentyl or cyclohexyl, each of which is optionally mono- to hexasubstituted by fluorine, chlorine, bromine, cyano, carboxyl, methyl, ethyl, methoxy, ethoxy, n- or i-propyl, methoxy-carbonyl or ethoxycarbonyl; or represents optionally mono- to trisubstituted phenyl, naphthyl, benzyl, phenethyl, furyl, benzofuranyl, pyrrolyl, indolyl, thienyl, benzothienyl, | oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i- propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, or trifluromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxximinomethyl, hydroximinoethyl, methoximinomethyl, ethoximinomethyl, and ethoximinoethyl;

trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl; and cyclopropyl, cyclobutyl, cyclopentyl or cyclohexyl.

3. A compound of the formula (I) according to claim 1, in which

| | |
|---|---|
| A | represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methylpropylene), each of which is optionally mono- or polysubstituted by identical or different substituents from the group consisting of fluorine, chlorine, cyano, methoxy, phenyl, tolyl, ethylphenyl, methoxyphenyl, ethoxyphenyl, chlorophenyl, fluorophenyl, trifluoromethylphenyl or xylyl; |
| $Q^1, Q^2, Q^3$ | are identical or different and each represent oxygen or sulphur; |
| $R^1$ | represents methyl, ethyl, n- or i-propyl, n-, i-, s- or t-butyl, each of which is optionally mono- to trisubstituted by fluorine, chlorine, bromine, methoxy, ethoxy, methylthio, or each of which is optionally substituted by fluorine and/or chlorine; or |
| | represents allyl, crotonyl, 1-methyl-allyl, propargyl or 1-methyl-propargyl, each of which is optionally mono- to trisubstituted by fluorine, or chlorine; or |
| | represents cyclobutyl, cyclopentyl or cyclohexyl, each of which is optionally mono- to hexasubstituted by fluorine, chlorine, bromine, methoxy, ethoxy1 phenyl, which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy, methyl, ethyl, n- or i- propyl; or |
| | represents optionally mono- to trisubstituted phenyl, naphthyl, benzyl, furyl, benzofuranyl, thienyl, benzothienyl, pyridyl, quinolyl, tetrahydrofuryl, or perhydropyranyl, the substituents being selected from the group consisting of: |
| | fluorine, chlorine, bromine, cyano, nitro, methyl, ethyl, n- or i-propyl, n-, i-, s- or t-butyl, methoxy, ethoxy, n- or i- propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl; and |
| | trimethylene (propane-1,3-diyl), methylenedioxy or ethylenedioxy each of which is attached twice and each of which is optionally mono- or polysubstituted by identical or different substituents from the group consisting of fluorine, chlorine, methyl, trifluoromethyl, ethyl, n- and i-propyl; |
| $R^2, R^5$ | are identical or different and each represent hydrogen or represent methyl; |
| $R^3$ | represents hydrogen or represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, |

| | |
|---|---|
| | methylthio, ethylthio, methylsulphinyl, ethylsulphinyl, methylsulphonyl, ethylsulphonyl, or ethylsulphonyl, each of which is optionally substituted by fluorine and/or chlorine; or represents allyl, crotonyl, 1-methyl-allyl, propargly or 1-methyl-propargyl, each of which is optionally mono- to trisubstituted by fluorine, chlorine or bromine; or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; |
| $R^4$ | represents methyl, ethyl, n- or i-propyl, n-, i-, s- or t-butyl, each of which is optionally mono- to pentasubstituted by fluorine, chlorine, bromine, cyano, hydroxyl, amino, methoxy, ethoxy, methylthio, ethylthio, methylsulphinyl, ethylsulphinyl, methylsulphonyl, or ethylsulphonyl, each of which is optionally substituted by fluorine and or chlorine; or represents allyl, crotonyl, 1-methyl-allyl, propargyl or 1-methyl-propargly, each of which is optionally mono- to trisubstituted by fluorine, chlorine or bromine; or represents cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; |
| $R^3$ and $R^4$ | together with the carbon atom to which they are attached represent cyclopropyl, cyclobutyl, cyclopentyl or cyclohexyl, each of which is optionally mono- to hexasubstituted by fluorine, chlorine, bromine, cyano, carboxyl, methyl, ethyl, n- or i-propyl, methoxy-carbonyl or ethoxy-carbonyl; and |
| $R^6$ | represents cyclopropyl, cyclobutyl, cyclopentyl or cyclohexyl, each of which is optionally mono- to hexasubstituted by fluorine, chlorine, bromine, cyano, carboxyl, methyl, ethyl, methoxy, ethoxy, n- or i-propyl, methoxy-carbonyl or ethoxycarbonyl; or represents optionally mono- to trisubstituted phenyl, naphthyl, benzyl, phenethyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, the substituents being selected from the group consisting of: fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difuorochloromethylthio, trifluoromethylthio, trifluoromethylsulphinyl, or trifluromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxximinomethyl, hydroximinoethyl, methoximinomethyl, ethoximinomethyl, methoximinoethyl and ethoximinoethyl; trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl; and cyclopropyl, cyclobutyl, cyclopentyl or cyclohexyl. |

4. A compound of the formula (I) according to claim 1, in which

| | |
|---|---|
| A | represents a single bond or represents methylene, 1,1-ethylene, 1,2-ethylene 1,1-propylene, 1,2-propylene or 2,2-propylene; |
| $Q^1, Q^2, Q^3$ | each represent oxygen; |
| $R^1$ | represents methyl, ethyl, n- or i-propyl, n-, i-, s- or t-butyl, cyclopentyl, cyclohexyl or represents optionally methyl-, ethyl-, methoxy-, ethoxy-, bromine-, chlorine- or fluorine-substituted phenyl or benzyl; |
| $R^2$ and $R^5$ | each represent hydrogen; |
| $R^3$ | represents hydrogen, methyl, ethyl or cyclopropyl; |
| $R^4$ | represents methyl, ethyl or cyclopropyl; or |
| $R^3$ and $R^4$ | together with the carbon atom that they are attached to form a cyclopentane or cyclohexane ring; and |
| $R^6$ | represents cyclohexyl which is in each case optionally mono- or disubstituted by methyl, ethyl, methoxy or ethoxy; or |

-continued represents phenyl, naphthyl, furyl, benzofuranyl, pyrrolyl, indolyl, thienyl, benzothienyl, pyridyl, quinolyl, pyrimidyl, pyridazinyl, pyrazinyl, each of which is optionally mono- to trisubstituted, the substituents selected from the group consisting of:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i- propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylafflino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl and ethoximinoethyl; and trimethylene (propane-1,3-diyl), methylenedioxy or ethylenedioxy, each of which is attached twice and each of which is optionally mono- or polysubstituted by identical or different substituents from the group consisting of fluorine, chlorine, methyl, trifluoromethyl, ethyl, n- and i-propyl.

5. A pesticidal composition comprising a pesticidally effective amount of at least one compound of the formula (I) according to claim 1 and a carrier.

6. A method for controlling pests comprising applying a pesticidally effective amount of a compound of the formula (I) according to claim 1 to said pests and/or their habitat.

7. A process for preparing a compound of the formula (I) according to claim 1, comprising reacting a N-substituted amino acid of the formula (II):

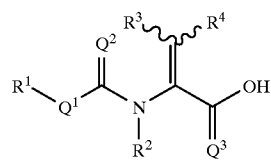
(II)

with an amine of the formula (III):

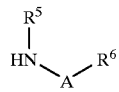
(III)

optionally in the presence of a reaction auxiliary and optionally in the presence of a diluent.

8. A compound of the formula (I):

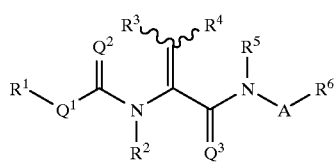
(I)

in which

| | |
|---|---|
| A | represents a single bond or alkylene |
| $Q^1, Q^2, Q^3$ | are identical or different and each represent oxygen or sulphur, |
| $R^1$ | represents optionally substituted alkyl, alkenyl, alkinyl, cycloalkyl, cycloalkenyl, arylalkyl, aryl, heterocyclylalkyl or heterocyclyl, |
| $R^2, R^5$ | are identical or different and each represent hydrogen or optionally substituted alkyl, |
| $R^3$ | represents hydrogen, or optionally substituted alkyl or cycloalkyl, |
| $R^4$ | represents, alkyl or optionally substituted cycloalkyl, or |
| $R^3$ and $R^4$ | together with the carbon atom that they are attached to form an optionally substituted carbocyclic ring; and |
| $R^6$ | represents optionally substituted cycloalkyl, cycloalkenyl, aryl or heterocyclyl; | with the exception of:

[1-[[[3,4-dioxo-2-(2-propenyloxy)-1-cyclobuten-1-yl] amino]carbonyl]-1-propenyl]-carbamic acid 1,1-dimethylethyl ester;

N-[2,3-didehydro-N-[(1,1-dimethylethoxy)carbonyl] norvalyl]-L-tyrosine methyl ester; and (Z)-2,3-didehydro-N-[(phenylmethoxy)carbonyl]-2-aminobutanoyl-L-tryptophan methyl ester.

9. A pesticidal composition comprising a pesticidally effective amount of at least one compound of the formula (I) according to claim 8 and a carrier.

10. A method for controlling pests comprising applying a pesticidally effective amount of a compound of the formula (I) according to claim 8 to said pests and/or their habitat.

11. A process for preparing a compound of the formula (I) according to claim 8, comprising reacting a N-substituted amino acid of the formula (II):

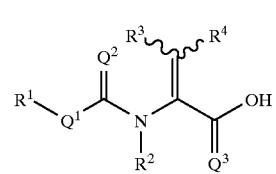
(II)

with an amine of the formula (III):
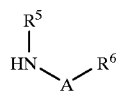
(III)
optionally in the presence of a reaction auxiliary and optionally in the presence of a diluent.
* * * * *